US010653640B2

(12) United States Patent
Small-Howard et al.

(10) Patent No.: US 10,653,640 B2
(45) Date of Patent: May 19, 2020

(54) CANNABINOID-CONTAINING COMPLEX MIXTURES FOR THE TREATMENT OF NEURODEGENERATIVE DISEASES

(71) Applicant: GROWBLOX LIFE SCIENCES L.L.C., Las Vegas, NV (US)

(72) Inventors: Andrea Small-Howard, Norwalk, CA (US); Helen Turner, Honolulu, HI (US)

(73) Assignee: GBS GLOBAL BIOPHARMA, INC., Ontario (CA)

( * ) Notice: Subject to any disclaimer, the term of this patent is extended or adjusted under 35 U.S.C. 154(b) by 378 days.

(21) Appl. No.: 15/729,565

(22) Filed: Oct. 10, 2017

(65) Prior Publication Data

US 2018/0098948 A1 Apr. 12, 2018

Related U.S. Application Data

(60) Provisional application No. 62/406,764, filed on Oct. 11, 2016.

(51) Int. Cl.

| *A61K 31/05* | (2006.01) |
|---|---|
| *A61K 31/015* | (2006.01) |
| *A61K 31/045* | (2006.01) |
| *A61K 31/352* | (2006.01) |
| *A61K 36/185* | (2006.01) |
| *A61P 25/28* | (2006.01) |
| *A61K 45/06* | (2006.01) |
| *A61K 9/00* | (2006.01) |

(52) U.S. Cl.
CPC ............ *A61K 31/05* (2013.01); *A61K 9/0073* (2013.01); *A61K 9/0078* (2013.01); *A61K 31/015* (2013.01); *A61K 31/045* (2013.01); *A61K 31/352* (2013.01); *A61K 36/185* (2013.01); *A61K 45/06* (2013.01); *A61P 25/28* (2018.01)

(58) Field of Classification Search
CPC .... A61K 31/05; A61K 31/015; A61K 31/045; A61K 31/352; A61K 36/185; A61K 45/06; A61P 25/28
USPC ........................................................ 514/454
See application file for complete search history.

(56) References Cited

U.S. PATENT DOCUMENTS

| 8,673,368 B2 | 3/2014 | Guy et al. |
|---|---|---|
| 2014/0228438 A1 | 8/2014 | Iuvone et al. |
| 2014/0243405 A1 | 8/2014 | Whalley et al. |
| 2014/0287068 A1* | 9/2014 | Lewis ................... A01G 22/00 424/725 |
| 2015/0343071 A1 | 12/2015 | Vangara et al. |
| 2016/0250270 A1 | 9/2016 | Wendschuh et al. |

FOREIGN PATENT DOCUMENTS

| WO | WO 2007/083098 A1 | 7/2007 |
|---|---|---|
| WO | WO 2010/127033 A1 | 11/2010 |
| WO | WO 2013/005017 A1 | 1/2013 |
| WO | WO 2013/045891 A1 | 4/2013 |
| WO | WO 2014/145490 A2 | 9/2014 |
| WO | WO 2015/025312 A1 | 2/2015 |
| WO | WO 2015/198078 A1 | 12/2015 |
| WO | WO 2017/193072 A1 | 11/2017 |

OTHER PUBLICATIONS

Cali, T. et al., "Calcium Signaling in Parkinson's Disease," Cell Tissue Res., 2014, pp. 439-454, vol. 357, No. 2.
Kang, S. et al., "Ca$_v$1.3-Selective L-Type Calcium Channel Antagonists as Potential New Therapeutics for Parkinson's Disease," Nature Communications, Article No. 1146, 2012, pp. 1-7.
PCT International Search Report and Written Opinion, PCT Application No. PCT/US2017/055989, dated Jan. 10, 2018, 14 pages.
Russo, E.B., "Taming THC: Potential Cannabis Synergy and Phytocannabinoid-Terpenoid Entourage Effects," British Journal of Pharmacology, dated Jul. 12, 2011, pp. 1344-1364, vol. 163, No. 7.
Izzo, A.A. et al., "Non-Psychotropic Plant Cannabinoids: New Therapeutic Opportunities from an Ancient Herb," Trends in Pharmacological Sciences, Oct. 1, 2009, pp. 515-527, vol. 30, No. 10.

* cited by examiner

*Primary Examiner* — Yevgeny Valenrod
(74) *Attorney, Agent, or Firm* — Fenwick & West LLP

(57) ABSTRACT

Provided herein are cannabinoid-containing complex mixtures suitable for use as active pharmaceutical ingredients. The complex mixtures comprise at least a first major cannabinoid, at least a first minor cannabinoid, and optionally at least a first selected terpene. Also provided are methods of making the complex mixtures; pharmaceutical compositions comprising the complex mixture, and methods of using the pharmaceutical compositions for the treatment of neurodegenerative diseases, including Alzheimer's disease, Parkinson's disease, Lewy Body Dementia, or Huntington's disease.

4 Claims, 10 Drawing Sheets

Figure 3B:
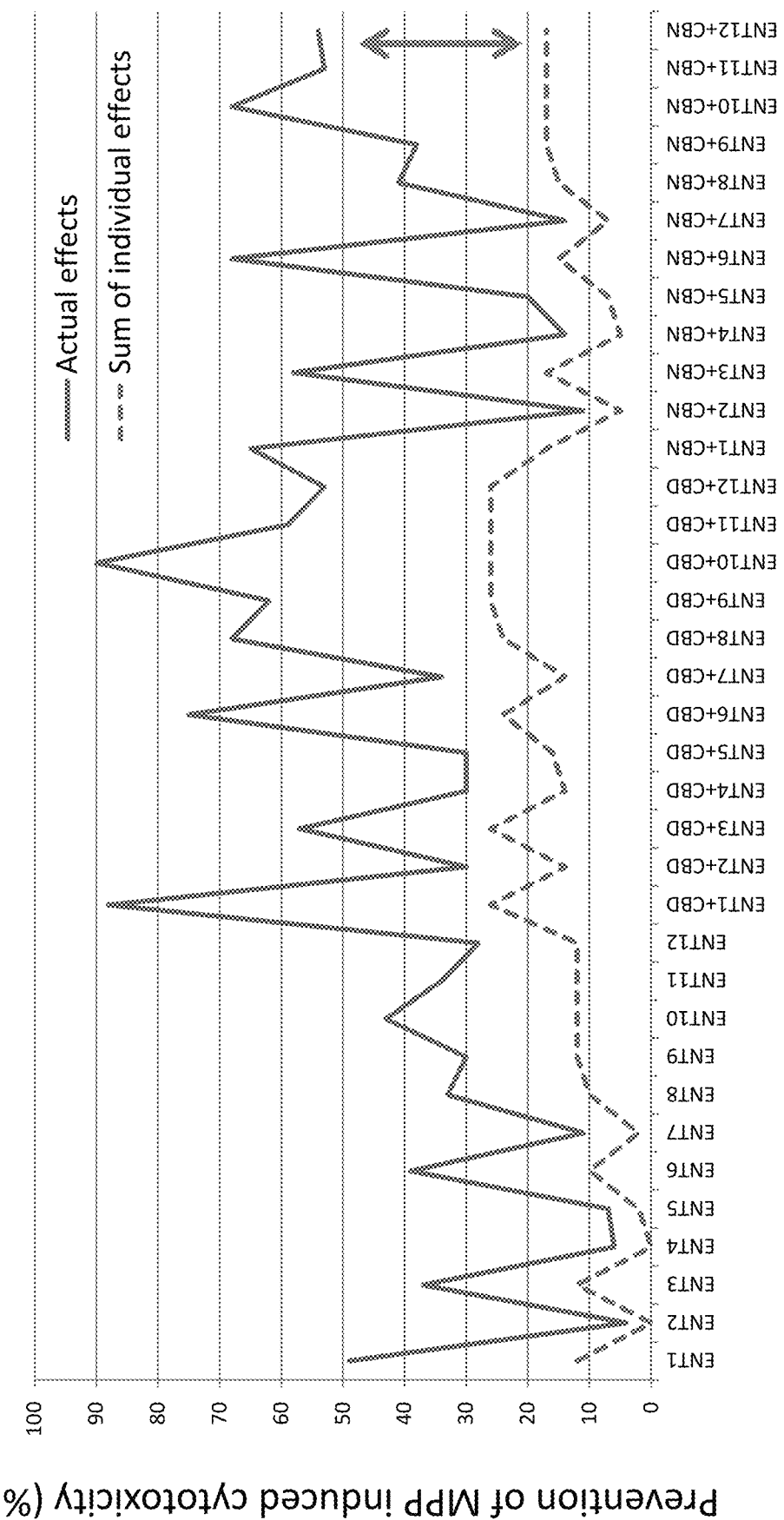

| | Tested Compounds | Concentration (μM) | Prevention of MPP induced cytotoxicity (%) (SD) |
|---|---|---|---|
| Control | None | 0 | 0 |
| Major Cannabinoid | Cannabidiol | 1 | 0 |
| | | 10 | 14 (2.5) |
| | | 100 | 18 (3.3) |
| | Cannabinol | 1 | 7 (0.3) |
| | | 10 | 5 (1.0) |
| | | 100 | 0 |
| Minor Cannabinoid | Cannabichromene | 1 | 0 |
| | | 10 | 0 |
| | | 100 | 3 (0.1) |
| | Cannabigerol | 1 | 0 |
| | | 10 | 2 (0.25) |
| | | 100 | 3 (1.1) |
| | Cannabidivarin | 1 | 9 (1.2) |
| | | 10 | 10 (1.3) |
| | | 100 | 14 (1.6) |

FIG. 1A

| Tested Compounds | Concentration (μM) | Prevention of MPP induced cytotoxicity |
|---|---|---|
| Limonene | 1 | 0 |
| | 10 | 0 |
| | 100 | 0 |
| Linalool | 1 | 0 |
| | 10 | 0 |
| | 100 | 0 |
| Nerolidol | 1 | 0 |
| | 10 | 0 |
| | 100 | 4 (0.2) |
| Pinene | 1 | 0 |
| | 10 | 0 |
| | 100 | 0 |
| Phytol | 1 | 0 |
| | 10 | 0 |
| | 100 | 0 |

Selected Terpenes

FIG. 1B

| | Sub-Mixtures |
|---|---|
| ENT1 | 3 Minor Cannabinoids (Cannabichromene/ Cannabigerol/ Cannabidivarin)<br>5 Selected Terpenes (Limonene/ Linalool/ Nerolidol/ Pinene/ Phytol) |
| ENT2 | 5 Selected Terpenes (Limonene/ Linalool/ Nerolidol/ Pinene/ Phytol) |
| ENT3 | 3 Minor Cannabinoids (Cannabichromene/ Cannabigerol/ Cannabidivarin) |
| ENT4 | 1 Minor Cannabinoid (Cannabichromene)<br>5 Selected Terpenes (Limonene/ Linalool/ Nerolidol/ Pinene/ Phytol) |
| ENT5 | 1 Minor Cannabinoid (Cannabigerol)<br>5 Selected Terpenes (Limonene/ Linalool/ Nerolidol/ Pinene/ Phytol) |
| ENT6 | 1 Minor Cannabinoid (Cannabidivarin)<br>5 Selected Terpenes (Limonene/ Linalool/ Nerolidol/ Pinene/ Phytol) |
| ENT7 | 2 Minor Cannabinoids (Cannabichromene/ Cannabigerol) |
| ENT8 | 2 Minor Cannabinoids (Cannabichromene/ Cannabidivarin) |
| ENT9 | 2 Minor Cannabinoids (Cannabigerol/ Cannabidivarin)<br>4 Selected Terpenes (Limonene/ Linalool/ Nerolidol/ Pinene/ Phytol) |
| ENT10 | 3 Minor Cannabinoids (Cannabichromene/ Cannabigerol/ Cannabidivarin)<br>2 Selected Terpenes (Limonene/ Linalool) |
| ENT11 | 3 Minor Cannabinoids (Cannabichromene/ Cannabigerol/ Cannabidivarin)<br>1 Selected Terpene (Nerolidol) |
| ENT12 | 3 Minor Cannabinoids (Cannabichromene/ Cannabigerol/ Cannabidivarin)<br>2 Selected Terpenes (Pinene/ Phytol) |

FIG. 2

|  | No Major Cannabinoid | | Major Cannabinoid | | | |
|---|---|---|---|---|---|---|
|  | | | Cannabidiol (10µM) | | Cannabinol (10µM) | |
|  | Sum of Individual effects | Actual Effects | Sum of Individual effects | Actual Effects | Sum of Individual effects | Actual Effects |
| ENT1 | 12 | 37 (3.8) | 26 | 62 (3.1) | 17 | 48 (2.1) |
| ENT2 | 0 | 4 (1.1) | 14 | 16 (3.0) | 5 | 6 (0.1) |
| ENT3 | 12 | 25 (0.5) | 26 | 31 (2.2) | 17 | 41 (4.6) |
| ENT4 | 0 | 6 (0.7) | 14 | 16 (2.2) | 5 | 9 (0.4) |
| ENT5 | 2 | 5 (1.0) | 16 | 14 (2.9) | 7 | 13 (1.6) |
| ENT6 | 10 | 29 (3.4) | 24 | 51 (4.4) | 15 | 53 (2.5) |
| ENT7 | 2 | 9 (2.1) | 14 | 20 (2.0) | 7 | 7 (1.2) |
| ENT8 | 10 | 23 (1.3) | 24 | 44 (3.9) | 15 | 26 (2.7) |
| ENT9 | 12 | 18 (1.5) | 26 | 36 (2.7) | 17 | 21 (1.9) |
| ENT10 | 12 | 31 (0.7) | 26 | 64 (6.2) | 17 | 51 (1.4) |
| ENT11 | 12 | 22 (1.8) | 26 | 33 (2.6) | 17 | 36 (2.4) |
| ENT12 | 12 | 16 (0.9) | 26 | 27 (2.6) | 17 | 37 (3.6) |

FIG. 3A    Prevention of MPP induced cytotoxicity (% (SD))

| | Major Cannabinoid | | |
|---|---|---|---|
| | No Major Cannabinoid | Cannabidiol (10µM) | Cannabinol (10µM) |
| ENT1 | 131 | 146 | 131 |
| ENT2 | 101 | 107 | 106 |
| ENT3 | 121 | 118 | 114 |
| ENT4 | | | |
| ENT5 | | | |
| ENT6 | 115 | 122 | 118 |
| ENT7 | | | |
| ENT8 | 119 | 138 | |
| ENT9 | | | |
| ENT10 | 113 | 116 | 118 |
| ENT11 | 111 | 103 | 104 |
| ENT12 | | | |

Dopamine secretion relative to PMA/Iono induced dopamine secretion (%)

FIG. 4

CANNABINOID-CONTAINING COMPLEX MIXTURES FOR THE TREATMENT OF NEURODEGENERATIVE DISEASES

1. CROSS-REFERENCE TO RELATED APPLICATIONS

This application claims priority benefit to U.S. Provisional Application No. 62/406,764, filed Oct. 11, 2016, which is incorporated by reference in its entirety.

2. BACKGROUND

In an aging population, neurodegeneration associated with Parkinson's disease, Alzheimer's disease, Lewy Body Dementia, and Huntington's disease is a growing health burden.

Among these neurodegenerative disorders, the pathophysiology of Parkinson's disease (PD) has been particularly well studied.

Mechanistically, the motor symptoms of PD are linked to death of dopamine-producing neurons in the midbrain's substantia nigra and to the deposition of Lewy bodies in various brain regions. Desensitization of the dopamine response system has also been documented, suggesting that both production and efficacy of dopamine are compromised in the disease. Most of the existing agents currently approved for treating PD address symptoms of dopamine depletion, such as bradykinesia, and do not modify disease progression.

Mitochondrial function is central to PD pathogenesis. In the 1980s, users of the illicit drug MPTP (1-methyl-4-phenyl-1,2,3,6-tetrahydropyridine), a mitochondrial electron transport chain complex I inhibitor, developed PD. Their symptoms and eventual autopsy findings recapitulated aspects of PD. While Lewy bodies were noticeably absent (also a finding in MPTP-treated primates), dopamine therapy was transiently successful, indicating that the other arm of the PD pathology was a feature of MPTP exposure. Since these studies, a wealth of literature has affirmed the linkage between mitochondria, specifically oxidation, and PD. In addition, mitochondrial Complex I and III have been implicated, and the linkage between their production of reactive oxygen species and oxidative stress in the PD brain/dopaminergic neurons has been elucidated.

Cannabinoids have been suggested as potential agents for treating a spectrum of neurological disorders, including PD.

A priori, cannabinoids would appear to be promising drugs for targeting the mechanistic pathways that underlie PD, and potentially modifying disease progression. First, they are clearly capable of acting as anti-oxidants, specifically opposing oxidative stress at the mitochondrion. Second, cannabinoid receptors are located in the brain regions compromised in PD, with the globus pallidus and substantia nigra pars reticulate showing some of the highest CB1 receptor expression levels in the brain, and also expressing the ionotropic cannabinoid receptor TRPV1. Third, cannabinoids are pro-survival factors in neurons, and protect against oxidatively-induced cell death. There is even evidence that isolated cannabinoid compounds can act as anti-aggresomal factors, with delta-9 tetra-hydrocannabinol (THC) binding directly to Aß plaque peptides in Alzheimer's disease and causing disaggregation. Cannabinoids are pro-clearance, encouraging autophagy and dissolution of inclusion bodies.

Taken together, these functions of the endo-cannabinoid system position their exogenous counterparts extremely well as theoretical intervention strategies in pathological brain aging. Indeed, CB1-deficient mice display early onset of cognitive decline and the histological and molecular features that are common to PD, and smoked and ingested marijuana has been associated with both transient and sustained improvement in motor function, decreased pain and improved motor function in anecdotal reports of patient experiences.

Although a number of cannabinoids have been tested individually or in pairs, the tested cannabinoid compositions have not demonstrated the predicted therapeutic effects, and in particular, have not proven comparable in efficacy to the use of the whole *Cannabis* plants. This may be due to the complexity of compounds present in each *Cannabis* plant, coupled with the huge variability existing in various *Cannabis* strains. It is also possible that minor components of *Cannabis* plants (cannabinoids and other naturally occurring components) contribute positively or negatively to the overall therapeutic effects.

A number of research studies suggest that effective therapeutics for PD should target not only restoration of dopamine production, but also address calcium-overload induced cell death. See, e.g., Cali et al., *Cell Tissue Res.* 357(2):439-54 (2014); Kang et al., *Nature Communications* 3, Article number: 1146 (2012). *Cannabis* mixtures that contain ligands for cation channels (such as TRPV1) may be of limited therapeutic potential if these calcium-overload inducing components are not identified and removed.

Thus, there is a continuing need for novel and validated pharmacological agents for the treatment of PD and other neurodegenerative diseases. There is a particular need for well-defined compositions of cannabinoids that are effective for the treatment of PD and other neurodegenerative diseases.

3. SUMMARY

The present invention provides new cannabinoid-containing complex mixtures suitable for use as active pharmaceutical ingredients, methods of making the complex mixtures, and pharmaceutical compositions comprising the complex mixtures. The invention further relates methods of their use for the treatment of neurodegenerative diseases.

One aspect of the present invention relates to a pharmaceutically active ingredient comprising at least a first major cannabinoid; at least a first minor cannabinoid; and optionally, at least a first selected terpene. In some embodiments, the first major cannabinoid is cannabidiol (CBD). In some embodiments, the first major cannabinoid is cannabinol (CBN).

In some embodiments, the first minor cannabinoid is cannabidivarin. In some embodiments, the ingredient further comprises a second minor cannabinoid, and the second minor cannabinoid is cannabichromene. In some embodiments, the second minor cannabinoid is cannabigerol. In some embodiments, the ingredient comprises a third minor cannabinoid, and the third minor cannabinoid is cannabichromene.

In some embodiments, the ingredient further comprises at least a first selected terpene. In some embodiments, the active ingredient further comprises a second selected terpene. In some embodiments, the first and second terpenes are limonene and linalool. In some embodiments, the first and second terpenes are pinene and phytol. In some embodiments, the active ingredient comprises limonene, linalool, nerolidol, pinene, and phytol.

In some embodiments, the active ingredient is substantially free of THC and is therefore of limited or no demonstrable psychoactivity.

In some embodiments, the major cannabinoids, minor cannabinoids, and optional selected terpenes collectively constitute at least 75%, 80%, 85%, 90%, or 95% by weight of the active ingredient.

In some embodiments, all compounds in the active ingredient other than the major cannabinoids, the minor cannabinoids, and the selected terpenes are extractable from *Cannabis sativa*.

In some embodiments, the major cannabinoids collectively constitute 5-40% by weight of the active ingredient; the minor cannabinoids collectively constitute 5-70% by weight of the active ingredient; and the selected terpenes collectively constitute 0-70% by weight of the active ingredient.

In some embodiments, the major cannabinoids collectively constitute 10-35% by weight of the active ingredient; the minor cannabinoids collectively constitute 30-70% by weight of the active ingredient; and the selected terpenes collectively constitute 0-50% by weight of the active ingredient.

Another aspect of the present invention relates to a method of making a pharmaceutically active ingredient by adding at least a first major cannabinoid; adding at least a first minor cannabinoid; and optionally, adding at least a first selected terpene. In some embodiments, the first major cannabinoid, the first minor cannabinoid, and the optional first selected terpene is added to a *Cannabis sativa* extract. In some embodiments, the method further comprises a preceding step of measuring the concentration, and/or calculating the specific activity in the *Cannabis sativa* extract of each major cannabinoid, minor cannabinoid, and selected terpene.

In some embodiments, the first major cannabinoid, the first minor cannabinoid, or the optional first selected terpene is added to achieve a predetermined concentration in the active ingredient.

In some embodiments, the method further comprises a preceding step of preparing the *Cannabis sativa* extract. In some embodiments, the *Cannabis sativa* extract is prepared from a selected *Cannabis sativa* strain.

Another aspect of the present invention relates to a pharmaceutically active ingredient produced by the methods.

The present invention further relates to a pharmaceutical composition comprising the pharmaceutically active ingredient, and pharmaceutically acceptable carrier or diluent.

In some embodiments, the pharmaceutical composition is an oil, an emulsion, a gel, or an aerosol.

In some embodiments, the pharmaceutical composition is formulated for administration by inhalation, vaporizer, nebulizer, or aerosolizer.

In some embodiments, the pharmaceutical composition is formulated for oral, buccal, or sublingual administration.

In some embodiments, the pharmaceutical composition is formulated for intravenous, intramuscular, or subcutaneous administration. In some embodiments, the pharmaceutical composition is formulated for intrathecal or intracerebroventricular administration.

In some embodiments, the pharmaceutical composition is formulated for topical administration.

In some embodiments, the active ingredient is present in the pharmaceutical composition at a concentration of at least 0.01, 0.1, 0.5, or 1 mg/ml.

Another aspect of the present invention relates to a method of treating neurodegenerative disease by administering an effective amount of the pharmaceutical composition disclosed herein to a patient having a neurodegenerative disease. In some embodiments, the neurodegenerative disease is Alzheimer's disease, Parkinson's disease, Lewy Body Dementia, or Huntington's disease.

In some embodiments, the pharmaceutical composition is administered by inhalation. In some embodiments, the pharmaceutical composition is administered orally. In some embodiments, the pharmaceutical composition is administered by buccal administration. In some embodiments, the pharmaceutical composition is delivered by sublingual administration. In some embodiments, the pharmaceutical composition is administered by injection. In some embodiments, the pharmaceutical composition is administered by topical application.

In some embodiments, the pharmaceutical composition is administered in an amount sufficient to modulate survival of neurons or dopamine release.

In some embodiments, the major cannabinoid is administered in an amount of less than 1 g, 500 mg, 100 mg, or 10 mg per dose.

In some embodiments, the pharmaceutical composition is administered p.r.n., once a day, 2-4 times a day, 2-4 times a week, once a week or once every two weeks.

These and other aspects of the invention are described in further detail below.

4. BRIEF DESCRIPTION OF THE DRAWINGS

FIG. 1A tabulates data from Example 1 illustrating protective effects of individual major cannabinoids and minor cannabinoids against neuronal cell death induced by 1-methyl-4-phenylpyridinium (MPP). The protective effects are presented as % rescue from MPP-induced cell death as compared to a control. Each data point represents an average of twenty four (8×3) independent experiments conducted at a specific concentration (1, 10, or 100 µM) of each major or minor cannabinoid. Standard deviations are presented in brackets.

FIG. 1B tabulates data from Example 1 illustrating protective effects of individual selected terpenes. The data are presented as described above in FIG. 1A.

FIG. 2 identifies the composition of sub-mixtures tested in Example 1 (ENT 1-12). Each compound, whether minor cannabinoid or selected terpene, is present at an equal molar concentration in the ENT compositions.

FIG. 3A provides data from Example 1 illustrating protective effects of different sub-mixtures, ENT 1-12, with or without major cannabinoid (cannabidiol or cannabinol), against MPP-induced cell death.

FIG. 3B provides the same set of data presented in FIG. 3A as a line graph. The X-axis represents tested mixtures comprising one of the sub-mixtures (ENT 1-12) with or without major cannabinoid (CBD or CBN). The Y-axis represents % rescue from MPP-induced cell death compared to the control.

FIG. 4 provides data from Example 2 illustrating effects of sub-mixtures (ENT 1-12) with or without major cannabinoid (CBD or CBN) on stimulation of dopamine release. The amounts of dopamine release measured in response to different compositions are presented as % compared to the amount of dopamine release in response to a known secretagogue combination, PMA/Ionomycin.

Figure 5:
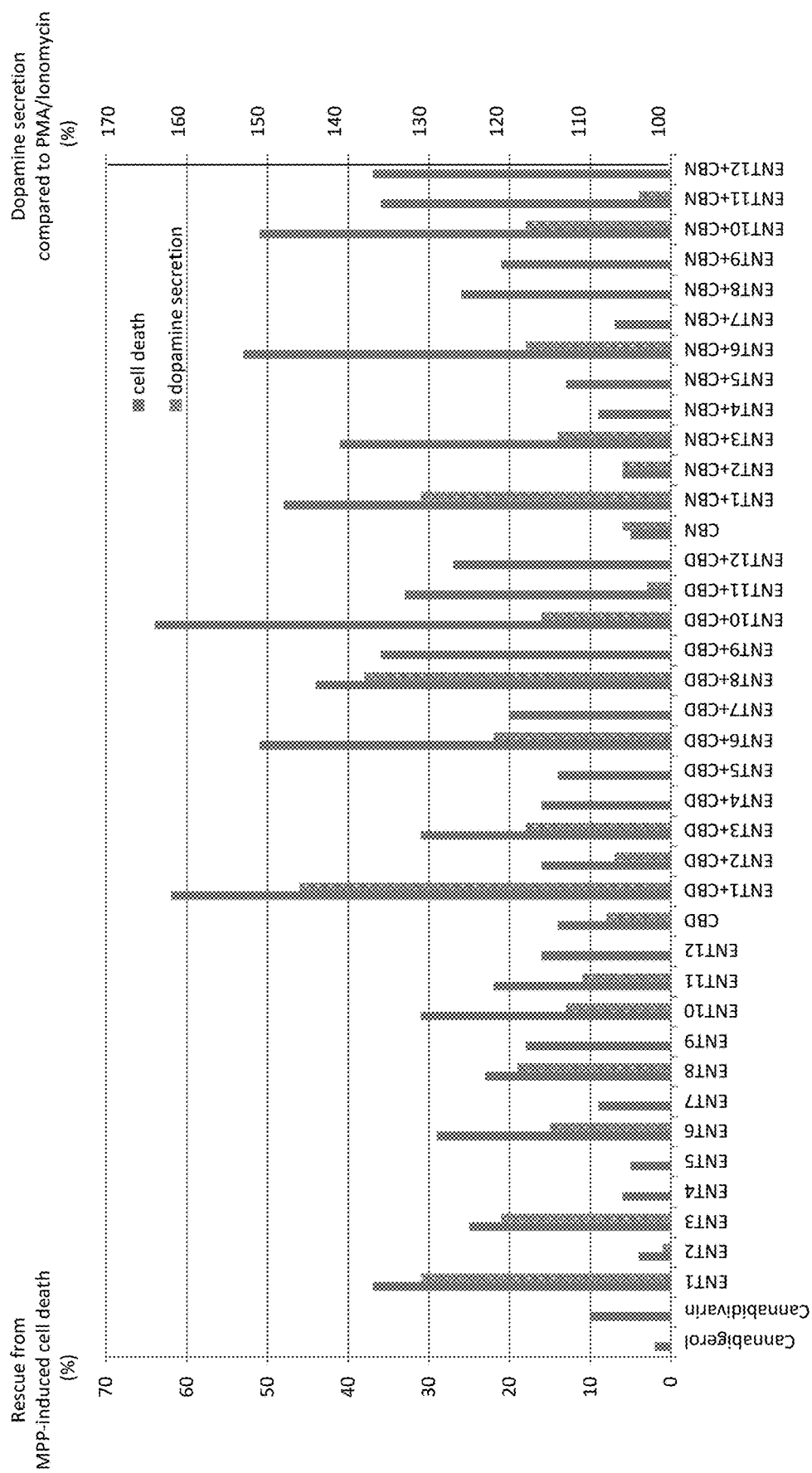

FIG. 5 provides a bar graph comparing results from Example 1 and Example 2, summarizing protective effect against MPP-induced cell death (solid bars) and effect on dopamine release (dotted bars) of the different compositions presented in FIGS. 2A-4. The solid bars represent % rescue from MPP-induced cell death compared to the control (y-axis on the left). The dotted bars represent the amount of dopamine release as % compared to the amount of dopamine release in response to PMA/Ionomycin (y-axis on the right).

Figure 6A:
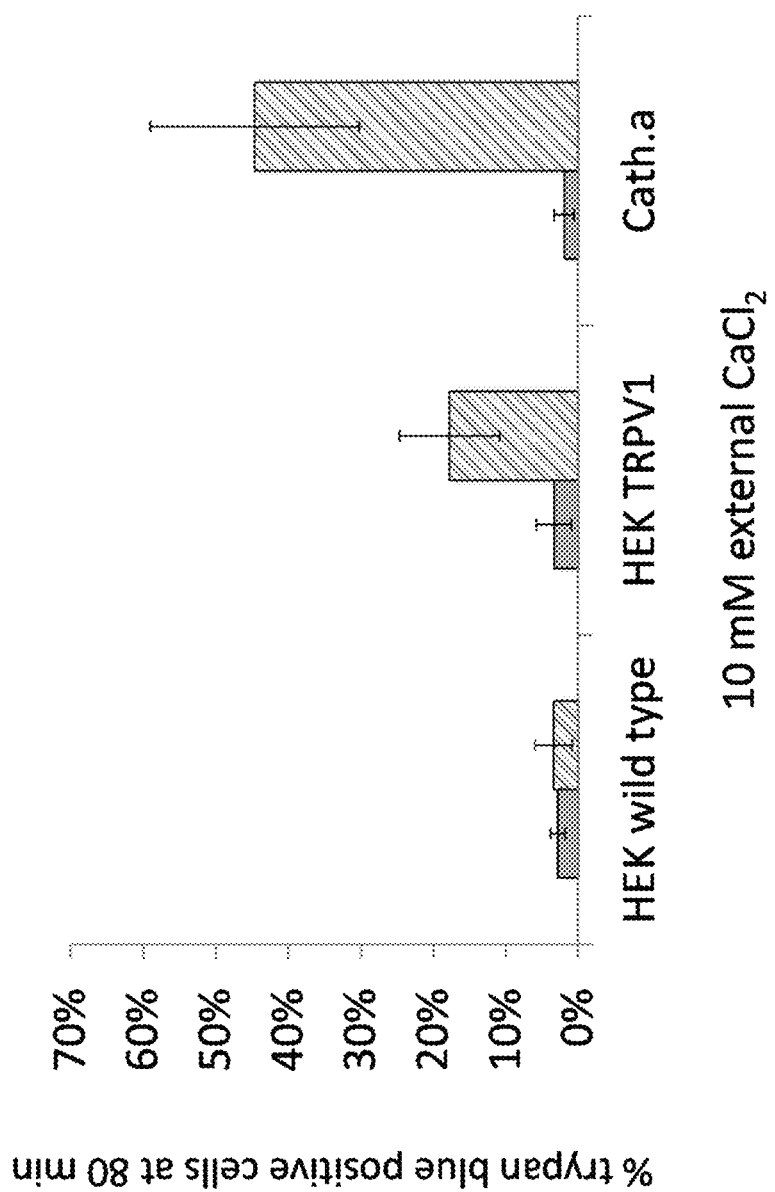
Figure 6B:
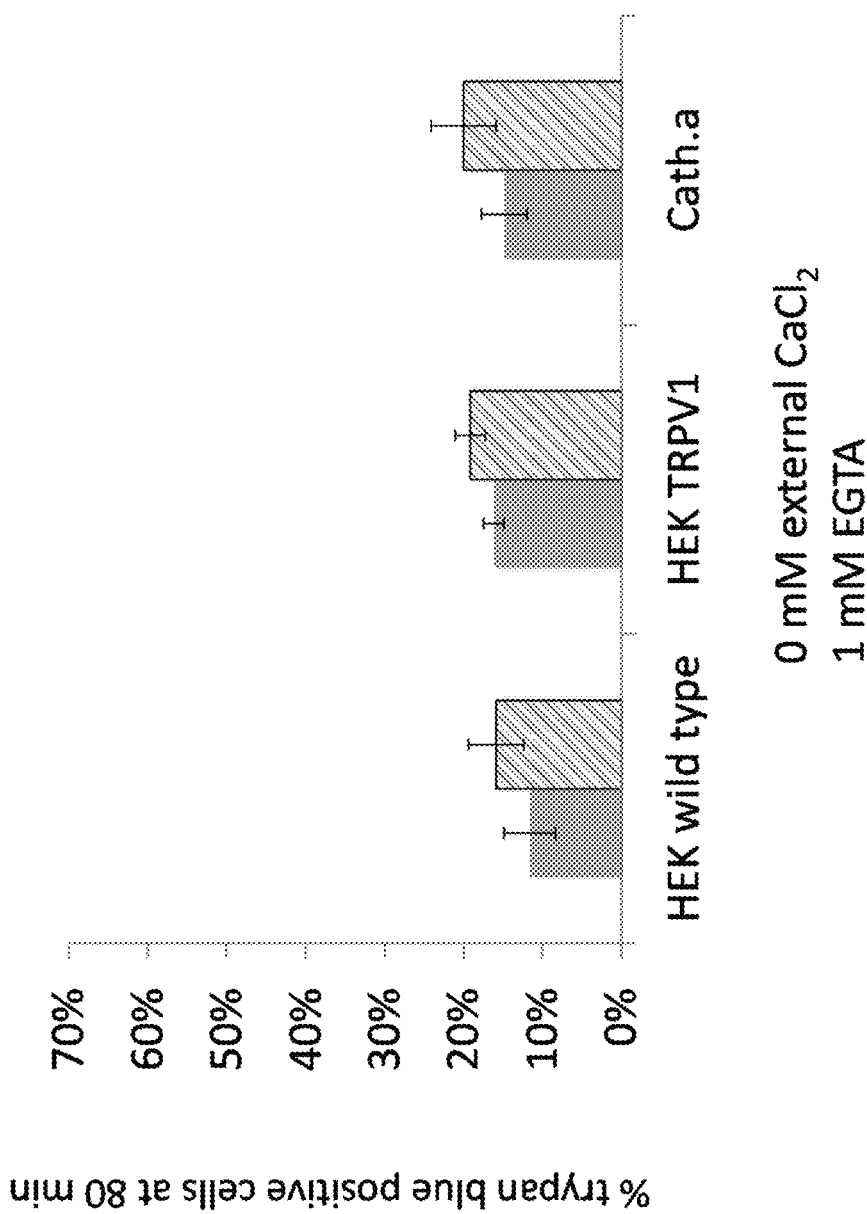

FIGS. 6A and 6B show that TRPV1 can mediate calcium-dependent cell death in Cath.a neurons. FIG. 6A graphs cell death (measured by trypan blue positivity) at 80 min in the presence of 10 mM external $CaCl_2$ in HEK wild type cells, HEK cells transfected with a TRPV1 expression construct, and Cath.a cells, in each case in the absence of stimulation (left bar) and 80 minutes after stimulation with 250 nM capsaicin (right bar), showing that capsaicin can induce cell death in Cath.a cells. FIG. 6B graphs cell death (percent trypan blue positive cells) at 80 minutes in the absence of external calcium in HEK wild type cells, HEK cells transfected with a TRPV1 expression construct, and Cath.a cells, in each case in the absence of stimulation (left bar) and 80 minutes after stimulation with 250 nM capsaicin (right bar), demonstrating that capsaicin-induced death of Cath.a cells is dependent upon the presence of external calcium.

Figure 7:
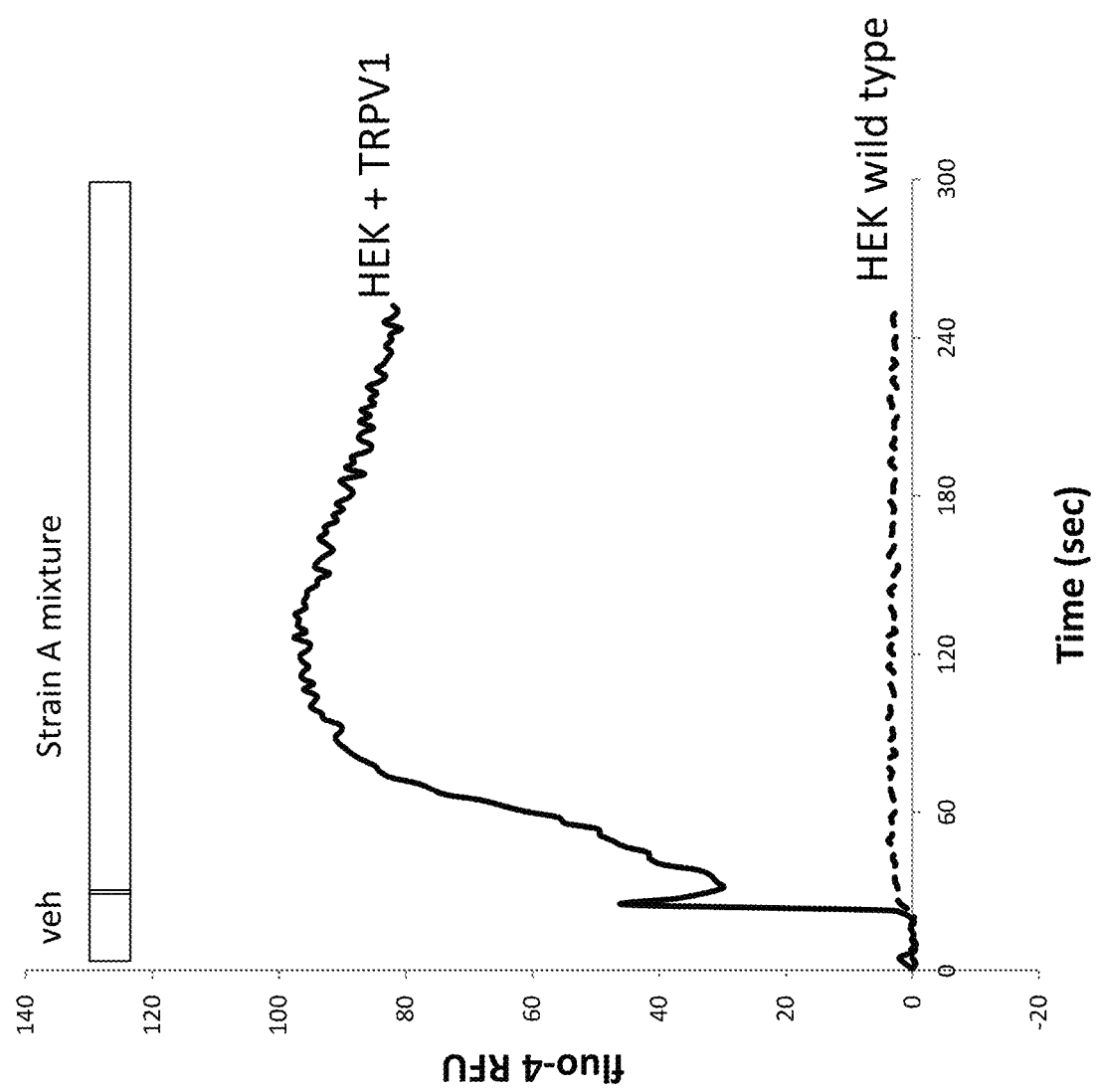

FIG. 7 demonstrates that a mixture of cannabinoids and terpenes modeled on the actual chemo-profile of a *Cannabis sativa* cultivar currently used medicinally in Nevada, USA, but modified to omit the psychoactive cannabinoids THC and THCA ("Strain A Mixture"), induces significant TRPV1-mediated calcium entry. In conjunction with the data presented in FIGS. 6A and 6B, these data demonstrate that cannabinoid-containing complex mixtures for the treatment of neurodegenerative diseases, and in particular cannabinoid-containing complex mixtures intended to preserve dopaminergic cell function and viability, should preferentially omit or contain at reduced levels cannabinoids and terpenes that trigger TRPV1-dependent calcium influx.

The figures depict various embodiments of the present invention for purposes of illustration only. One skilled in the art will readily recognize from the following discussion that alternative embodiments of the structures and methods illustrated herein may be employed without departing from the principles of the invention described herein.

5. DETAILED DESCRIPTION

5.1. Definitions

Unless defined otherwise, all technical and scientific terms used herein have the meaning commonly understood by a person skilled in the art to which this invention belongs. As used herein, the following terms have the meanings ascribed to them below.

"Major cannabinoid" means cannabidiol (CBD) or cannabinol (CBN). The major cannabinoid can be obtained by chemical synthesis, chemical modification, or obtained from plant materials derived from one or more *Cannabis* plants.

"Minor cannabinoid" means cannabichromene, cannabigerol, or cannabidivarin. The minor cannabinoid can be obtained by chemical synthesis, chemical modification, or obtained from plant materials derived from one or more *Cannabis* plants.

"Selected terpene" means limonene, linalool, nerolidol, pinene, or phytol. The selected terpene can be obtained by chemical synthesis, chemical modification, commercially, or obtained from plant materials derived from one or more *Cannabis* plants.

A "sub-mixture", or "ENT", is a mixture comprising a plurality of compounds selected from minor cannabinoids and/or selected terpenes as defined herein. FIG. 2 provides specific compositions of sub-mixtures, ENT 1-12, tested in the Examples presented herein.

A "cannabinoid-containing complex mixture" is a composition comprising a major cannabinoid and a sub-mixture (ENT).

A pharmaceutically active ingredient is "substantially free of THC" if the ingredient contains less than 0.3% (w/v) of delta-9 tetrahydrocannabinol. A pharmaceutical composition comprising a pharmaceutically active ingredient is "substantially free of THC" if the pharmaceutical composition contains less than 0.3% (w/v) of delta-9 tetrahydrocannabinol.

A "*Cannabis sativa* extract" is a composition obtained from *Cannabis sativa* plant materials by fluid and/or gas extraction, for example by supercritical fluid extraction (SFE) with $CO_2$. The *Cannabis sativa* extract typically contains major cannabinoids, minor cannabinoids, selected terpenes, and also other terpenes, phytocannabinoids, and secondary metabolites. For example, the *Cannabis sativa* extract can include one or more of bisabolol, humulene, terpinene, caryophyllene, camphene, geraniol, guaiol, isopulegoll, ocimene, cymene, eucalyptol, terpinolene, and myrcene.

5.2. Other Interpretational Conventions

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless otherwise indicated, reference to a compound that has one or more stereocenters intends each stereoisomer, and all combinations of stereoisomers, thereof.

5.3. Overview of Experimental Results

As described more fully in Example 1, we tested the neuroprotective effects of (i) each major cannabinoid, (ii) each minor cannabinoid, (iii) each selected terpene, (iv) sub-mixtures (ENT) 1-12, and (v) each ENT mixture in combination with each of the two major cannabinoids in an in vitro assay that is commonly used to identify agents capable of modifying the progression of neurodegeneration in Parkinson's disease.

Major and minor cannabinoids, used alone, showed some modest neuroprotective effects at 10 μM or 100 μM concentrations. However, most of the selected terpenes did not show any detectable neuroprotective effects, even at 100 μM concentration.

In contrast, our data demonstrated synergistic effects of certain sub-mixtures when applied in the absence of a major cannabinoid.

For example, ENT8 (cannabichromene and cannabidivarin) without a major cannabinoid reduced MPP-induced cytotoxicity by 23%, while the calculated sum of protective effects of its individual ingredients was only 10%. Analogously, ENT1 (comprising all 3 minor cannabinoids and all 5 selected terpenes) reduced MPP-induced toxicity by 37%, while the sum of effects of its individual ingredients was 12%. ENT10 (all 3 minor cannabinoids and two selected terpenes, limonene and linalool) reduced MPP-induced toxicity by 31%, while the sum of rescue effects of its individual ingredients is only 12%. The differences between the actual effects and the calculated sum of individual effects (see, double-head arrow in FIG. 3B) represents synergistic effects.

Even greater synergistic effects were observed when sub-mixtures were applied together with a major cannabinoid, with several compositions reducing MPP-induced cytotoxicity by more than 50%. For example, ENT10+cannabidiol reduces toxicity 64%; ENT1+cannabidiol reduces cytotoxicity 62%; ENT6+cannabidiol reduces cytotoxicity 51%; and ENT10+cannabinol provides 51% rescue. The degree of protection was significantly higher than the sum of individual effects: for example, the sum of individual ingredient effects was only 26% for ENT10+cannabidiol; 26% for ENT1+cannabidiol; 24% for ENT6+cannabidiol; and 17% for ENT10+cannabinol.

The tested compositions, prepared from pure compounds, were free of THC.

These data predict efficacy of certain cannabinoid-containing complex mixtures in preventing or reducing neurodegeneration in Parkinson's disease and other neurodegenerative disorders.

We selected certain compositions showing higher neuroprotective effects in Example 1 and in Example 2 tested their ability to stimulate dopamine release from PC12 cells.

Certain of the ENT sub-mixtures, alone and in combination with a major cannabinoid, significantly increased dopamine release. For example, as compared to secretion induced by a positive control, PMA/Ionomycin (for normalization, set to 100%), ENT1+cannabidiol increased secretion by 146%, ENT8+cannabidiol increased secretion 138%, ENT1 alone increased secretion 131%, and ENT1+cannabinol increased secretion 131%.

These data predict efficacy of certain cannabinoid-containing complex mixtures in treating symptoms of dopamine depletion in Parkinson's disease and other neurodegenerative disorders.

A number of research studies suggest that effective therapeutics for PD should target not only restoration of dopamine production, but also address calcium-overload induced cell death. See, e.g., Cali et al., *Cell Tissue Res.* 357(2):439-54 (2014); Kang et al., *Nature Communications* 3, Article number: 1146 (2012). As described in detail in Example 3, we demonstrated that TRPV1-mediated calcium influx can cause death of Cath.a catecholaminergic neurons in vitro, and demonstrated that a mixture of cannabinoids and terpenes modeled on the actual chemo-profile of a *Cannabis sativa* cultivar currently used medicinally in Nevada, USA (modified to omit the psychoactive cannabinoids THCA and THC) is capable of inducing significant TRPV1-mediated calcium entry. These data demonstrate that cannabinoid-containing complex mixtures for the treatment of neurodegenerative diseases, and in particular cannabinoid-containing complex mixtures intended to preserve dopaminergic cell function and viability, should be designed to omit or to contain at reduced levels cannabinoids and terpenes that trigger TRPV1-dependent calcium influx.

5.4. Pharmaceutically Active Ingredient

5.4.1. Major Cannabinoid, Minor Cannabinoid, Selected Terpene

Accordingly, in a first aspect, pharmaceutically active ingredients (also referred to herein synonymously as "active ingredient" and "active pharmaceutical ingredient") are provided that comprise at least a first major cannabinoid, at least a first minor cannabinoid, and optionally at least a first selected terpene.

In some embodiments, the first major cannabinoid is cannabidiol (CBD). In some embodiments, the first major cannabinoid is cannabinol (CBN). In some embodiments, the pharmaceutically active ingredient includes both cannabidiol and cannabinol.

In some embodiments, the first minor cannabinoid is cannabidivarin. In some embodiments, the first minor cannabinoid is cannabigerol. In some embodiments, the first minor cannabinoid is cannabichromene.

In some embodiments, the active ingredient further comprises a second minor cannabinoid.

In certain of these embodiments, the first minor cannabinoid is cannabidivarin and the second minor cannabinoid is cannabigerol. In certain of these embodiments, the first minor cannabinoid is cannabidivarin, and the second minor cannabinoid is cannabichromene.

In certain of these embodiments, the first minor cannabinoid is cannabigerol and the second minor cannabinoid is cannabidivarin. In certain of these embodiments, the first minor cannabinoid is cannabigerol and the second minor cannabinoid is cannabichromene.

In certain of these embodiments, the first minor cannabinoid is cannabichromene, and the second minor cannabinoid is cannabidivarin. In certain of these embodiments, the first minor cannabinoid is cannabichromene, and the second minor cannabinoid is cannabigerol.

In some embodiments, the active ingredient further comprises a third minor cannabinoid. In these embodiments, the active ingredient comprises cannabidivarin, cannabigerol, and cannabichromene.

In certain currently preferred embodiments, the first major cannabinoid is CBD, and the first minor cannabinoid is cannabidivarin. In other currently preferred embodiments, the first major cannabinoid is CBN, and the first minor cannabinoid is cannabidivarin. In some of these preferred embodiments, the ingredient further comprises a second minor cannabinoid. In certain of these embodiments, the second minor cannabinoid is cannabichromene. In certain of these embodiments, the second minor cannabinoid is cannabigerol.

In some embodiments, the active ingredient comprises at least a first selected terpene.

In some embodiments, the first selected terpene is limonene. In some embodiments, the first selected terpene is linalool. In some embodiments, the first selected terpene is nerolidol. In some embodiments, the first selected terpene is pinene. In some embodiments, the first selected terpene is phytol.

In some embodiments, the active ingredient further comprises a second selected terpene.

In certain of these embodiments, the first selected terpene is limonene, and the second selected terpene is linalool. In certain embodiments, the first selected terpene is limonene and the second selected terpene is nerolidol. In certain embodiments, the first selected terpene is limonene and the second selected terpene is pinene. In certain embodiments, the first selected terpene is limonene and the second selected terpene is phytol.

In certain of these embodiments, the first selected terpene is linalool, and the second selected terpene is limonene. In certain embodiments, the first selected terpene is linalool, and the second selected terpene is nerolidol. In certain embodiments, the first selected terpene is linalool, and the second selected terpene is pinene. In certain embodiments, the first selected terpene is linalool, and the second selected terpene is phytol.

In certain embodiments, the first selected terpene is nerolidol, and the second selected terpene is limonene. In certain embodiments, the first selected terpene is nerolidol and the second selected terpene is linalool. In certain embodiments, the first selected terpene is nerolidol, and the second selected terpene is pinene. In certain embodiments, the first selected terpene is nerolidol and the second selected terpene is phytol.

In certain embodiments, the first selected terpene is pinene, and the second selected terpene is limonene. In certain embodiments, the first selected terpene is pinene, and the second selected terpene is linalool. In certain embodiments, the first selected terpene is pinene, and the second selected terpene is nerolidol. In certain embodiments, the first selected terpene is pinene, and the second selected terpene is phytol.

In certain embodiments, the first selected terpene is phytol, and the second selected terpene is limonene. In certain embodiments, the first selected terpene is phytol, and the second selected terpene is linalool. In certain embodiments, the first selected terpene is phytol, and the second selected terpene is nerolidol. In certain embodiments, the first selected terpene is phytol and the second selected terpene is pinene.

In certain currently preferred embodiments, the first and the second selected terpenes are limonene and linalool. In some preferred embodiments, the first and the second selected terpenes are pinene and phytol.

In some embodiments, the active ingredients comprise 3, 4, or all 5 selected terpenes.

5.4.1.1. Relative Content

In typical embodiments, the major cannabinoids collectively constitute 5-40% by weight (wt %) of the active ingredient.

In certain embodiments, the major cannabinoids collectively constitute 5-10 wt % of the active ingredient, 10-15 wt % of the active ingredient, 15-20 wt % of the active ingredient, 20-25 wt % of the active ingredient, 25-30 wt % of the active ingredient, 30-35 wt % of the active ingredient, or 35-40 wt % of the active ingredient. In certain embodiments, the major cannabinoids collectively constitute at least 5 wt %, at least 10 wt %, at least 15 wt %, at least 20 wt %, at least 25 wt %, at least 30 wt %, at least 35 wt %, but each case no more than 40 wt %, of the active ingredient.

In typical embodiments, the minor cannabinoids collectively constitute 5-70% by weight of the active ingredient.

In certain embodiments, the minor cannabinoids collectively constitute 5-10 wt % of the active ingredient, 10-15 wt % of the active ingredient, 15-20 wt % of the active ingredient, 20-25 wt % of the active ingredient, 25-30 wt % of the active ingredient, 30-35 wt % of the active ingredient, or 35-40 wt % of the active ingredient. In certain embodiments, the minor cannabinoids collectively constitute 40-45 wt %, 45-50 wt %, 50-55 wt %, 55-60 wt %, 60-65 wt %, or 65-70 wt % of the active ingredient. In certain embodiments, the minor cannabinoids collectively constitute at least 5 wt %, 10 wt %, 15 wt %, 20 wt %, 25 wt %, 30 wt %, 35 wt %, 40 wt %, 45 wt % or 50 wt %, but in each case no more than 70 wt %, of the active ingredient In certain embodiments, the minor cannabinoids collectively constitute at least 55 wt %, at least 60 wt %, at least 65 wt %, but in each case less than 70 wt %, of the active ingredient.

In typical embodiments, the selected terpenes collectively constitute 0-70% by weight of the active ingredient. In embodiments in which at least one optional selected terpene is present, the selected terpenes collectively constitute 5-70 wt % of the active ingredient.

In certain embodiments, the selected terpenes collectively constitute at least 5 wt %, at least 10 wt %, at least 15 wt %, at least 20 wt %, at least 25 wt %, at least 30 wt %, at least 35 wt %, at least 40 wt %, at least 45 wt %, at least 50 wt %, at least 55 wt %, at least 60 wt %, or at least 65 wt %, but in each case less than 70 wt %, of the active ingredient.

In some currently preferred embodiments, the major cannabinoids collectively constitute 10-35% by weight of the active ingredient; the minor cannabinoids collectively constitute 30-70% by weight of the active ingredient; and the selected terpenes collectively constitute 0-50% by weight of the active ingredient.

In some embodiments, the major cannabinoids collectively constitute 5-40% (w/v) of the active ingredient.

In certain embodiments, the major cannabinoids collectively constitute 5-10% (w/v) of the active ingredient, 10-15% (w/v) of the active ingredient, 15-20% (w/v) of the active ingredient, 20-25% (w/v) of the active ingredient, 25-30% (w/v) of the active ingredient, 30-35% (w/v) of the active ingredient, or 35-40% (w/v) of the active ingredient. In certain embodiments, the major cannabinoids collectively constitute at least 5% (w/v), at least 10% (w/v), at least 15% (w/v), at least 20% (w/v), at least 25% (w/v), at least 30% (w/v), at least 35% (w/v), but each case no more than 40% (w/v), of the active ingredient.

In some embodiments, the minor cannabinoids collectively constitute 5-70% (w/v) of the active ingredient.

In certain embodiments, the minor cannabinoids collectively constitute 5-10% (w/v) of the active ingredient, 10-15% (w/v) of the active ingredient, 15-20% (w/v) of the active ingredient, 20 25% (w/v) of the active ingredient, 25-30% (w/v) of the active ingredient, 30-35% (w/v) of the active ingredient, or 35-40% (w/v) of the active ingredient. In certain embodiments, the minor cannabinoids collectively constitute 40-45% (w/v), 45-50% (w/v), 50-55% (w/v), 55-60% (w/v), 60-65% (w/v), or 65-70% (w/v) of the active ingredient. In certain embodiments, the minor cannabinoids collectively constitute at least 5% (w/v), 10% (w/v), 15% (w/v), 20% (w/v), 25% (w/v), 30% (w/v), 35% (w/v), 40% (w/v), 45% (w/v) or 50% (w/v), but in each case no more than 70% (w/v), of the active ingredient In certain embodiments, the minor cannabinoids collectively constitute at least 55% (w/v), at least 60% (w/v), at least 65% (w/v), but in each case less than 70% (w/v), of the active ingredient.

In some embodiments, the selected terpenes collectively constitute 0-70% (w/v) of the active ingredient. In embodiments in which at least one optional selected terpene is present, the selected terpenes collectively constitute 5-70% (w/v) of the active ingredient.

In certain embodiments, the selected terpenes collectively constitute at least 5% (w/v), at least 10% (w/v), at least 15% (w/v), at least 20% (w/v), at least 25% (w/v), at least 30% (w/v), at least 35% (w/v), at least 40% (w/v), at least 45% (w/v), at least 50% (w/v), at least 55% (w/v), at least 60% (w/v), or at least 65% (w/v), but in each case less than 70% (w/v), of the active ingredient.

In some currently preferred embodiments, the major cannabinoids collectively constitute 10-35% (w/v) of the active ingredient; the minor cannabinoids collectively constitute 30-70% (w/v) of the active ingredient; and the selected terpenes collectively constitute 0-50% (w/v) of the active ingredient.

5.4.1.2. Absolute Content

In some embodiments, the pharmaceutically active ingredient consists of major cannabinoids, minor cannabinoids, and selected terpenes. In these embodiments, the major cannabinoids, minor cannabinoids, and selected terpenes collectively constitute 100 wt % of the pharmaceutically active ingredient.

In some embodiments, the active ingredient consists essentially of major cannabinoids, minor cannabinoids, and selected terpenes.

In other embodiments, the major cannabinoids, minor cannabinoids, and selected terpenes collectively constitute less than 100% by weight (wt %) of the pharmaceutically active ingredient.

In some embodiments, the pharmaceutically active ingredient consists of major cannabinoids, minor cannabinoids, and selected terpenes. In these embodiments, the major cannabinoids, minor cannabinoids, and selected terpenes collectively constitute 100% (w/v) of the pharmaceutically active ingredient.

In some embodiments, the active ingredient consists essentially of major cannabinoids, minor cannabinoids, and selected terpenes.

In other embodiments, the major cannabinoids, minor cannabinoids, and selected terpenes collectively constitute less than 100% (w/v) of the pharmaceutically active ingredient.

5.4.2. Other Components

In some embodiments, the major cannabinoids, minor cannabinoids, and selected terpenes collectively constitute less than 100% by weight (wt %) of the pharmaceutically active ingredient.

In various such embodiments, the major cannabinoids, minor cannabinoids, and optional selected terpenes collectively constitute at least 75% by weight, but less than 100 wt %, of the pharmaceutically active ingredient. In specific embodiments, the major cannabinoids, minor cannabinoids, and optional selected terpenes collectively constitute at least 80%, at least at least 85%, at least 90%, at least 91%, at least 92%, at least 93%, at least 94%, or at least 95% by weight, but less than 100 wt %, of the active ingredient. In particular embodiments, the major cannabinoids, minor cannabinoids, and optional selected terpenes collectively constitute at least 96%, at least 97%, at least 98%, or at least 99% by weight, but less than 100 wt %, of the active ingredient.

In embodiments in which the major cannabinoids, minor cannabinoids, and selected terpenes collectively constitute less than 100% by weight (wt %) of the pharmaceutically active ingredient, the active ingredient further comprises compounds other than the major cannabinoids, minor cannabinoids, and selected terpenes. In typical such embodiments, all other compounds in the active ingredient are extractable from *Cannabis sativa*. In specific embodiments, all other compounds in the active ingredient are present in an extract made from *Cannabis sativa*.

In some embodiments, the major cannabinoids, minor cannabinoids, and selected terpenes collectively constitute less than 100% (w/v) of the pharmaceutically active ingredient.

In various such embodiments, the major cannabinoids, minor cannabinoids, and optional selected terpenes collectively constitute at least 75% (w/v), but less than 100% (w/v), of the pharmaceutically active ingredient. In specific embodiments, the major cannabinoids, minor cannabinoids, and optional selected terpenes collectively constitute at least 80%, at least at least 85%, at least 90%, at least 91%, at least 92%, at least 93%, at least 94%, or at least 95% (w/v), but less than 100% (w/v), of the active ingredient. In particular embodiments, the major cannabinoids, minor cannabinoids, and optional selected terpenes collectively constitute at least 96%, at least 97%, at least 98%, or at least 99% (w/v), but less than 100% (w/v), of the active ingredient.

In embodiments in which the major cannabinoids, minor cannabinoids, and selected terpenes collectively constitute less than 100% (w/v) of the pharmaceutically active ingredient, the active ingredient further comprises compounds other than the major cannabinoids, minor cannabinoids, and selected terpenes. In typical such embodiments, all other compounds in the active ingredient are extractable from *Cannabis sativa*. In specific embodiments, all other compounds in the active ingredient are present in an extract made from *Cannabis sativa*.

5.4.2.1. THC Content

In various embodiments, the active ingredient is substantially free of tetrahydrocannabinol (THC). These embodiments retain the therapeutic properties of the active pharmaceutical ingredient in treating neurodegenerative diseases and lacking psychoactive effects, offer certain regulatory and other advantages, In certain embodiments, the active ingredient is not substantially free of THC. In certain of these embodiments, the active ingredient comprises 1-10 percent by weight (wt %) THC. In specific embodiments, the active ingredient comprise 2-9 wt % THC, 3-8 wt % THC, 4-7 wt % THC. In certain embodiments, the active ingredient comprises 1, 2, 3, 4, 5, 6, 7, 8, 9 or 10 wt % THC.

In certain embodiments, the active ingredient is not substantially free of THC. In certain of these embodiments, the active ingredient comprises 1-10 percent (w/v) THC. In specific embodiments, the active ingredient comprise 2-9% (w/v) THC, 3-8% (w/v) THC, 4-7% (w/v) THC. In certain embodiments, the active ingredient comprises 1, 2, 3, 4, 5, 6, 7, 8, 9 or 10% (w/v) THC.

5.4.3. Process for Preparing Active Ingredient

In some embodiments, the pharmaceutically active ingredient is prepared by mixing chemically pure major cannabinoids, minor cannabinoids, and optional selected terpenes to desired final concentrations. Each of the major cannabinoids, minor cannabinoids, and selected terpenes can independently be chemically synthesized, either by total synthesis or by synthetic modification of an intermediate, purified from a compositional mixture such as a *Cannabis sativa* extract, or, as in the Examples described below, purchased commercially.

In other embodiments, the pharmaceutically active ingredient is prepared from a starting compositional mixture by adjusting to predetermined desired final concentrations any one or more of the major cannabinoids, minor cannabinoids, and optional selected terpenes. In typical embodiments, the starting compositional mixture is a *Cannabis sativa* extract. In currently preferred embodiments, the starting compositional mixture is a *Cannabis sativa* extract and one or more of the major cannabinoids, minor cannabinoids, and optional selected terpenes is added to the mixture to achieve predetermined desired final concentrations.

Typically in such embodiments, the process further comprises the earlier step of determining the concentration of each desired major cannabinoid, minor cannabinoid, and optional selected terpene in the starting compositional mixture.

In certain of these embodiments, the process further comprises the still earlier step of preparing a *Cannabis sativa* extract. Methods of preparing *Cannabis sativa* extracts are described in U.S. Pat. Nos. 6,403,126, 8,895,078, and 9,066,910; Doorenbos et al., Cultivation, extraction, and analysis of *Cannabis sativa* L., ANNALS OF THE NEW YORK ACADEMY OF SCIENCES, 191, 3-14 (1971); Fairbairn and Liebmann, The extraction and estimation of the cannabinoids in *Cannabis sativa* L. and its products, JOURNAL OF PHARMACY AND PHARMACOLOGY, 25, 150-155 (1973); Oroszlan and Verzar-petri, Separation, quantitation and isolation of cannabinoids from *Cannabis sativa* L. by overpressured layer chromatography, JOURNAL OF CHROMATOGRAPHY A, 388, 217-224 (1987), the disclosures of which are incorporated herein by reference in their entireties. In particular embodiments, the extraction method is chosen to provide an extract that has a content of major cannabinoids, minor cannabinoids, and selected terpenes that best approximates the predetermined composition of the active ingredient.

In some embodiments, the process further comprises a first step of selecting a *Cannabis sativa* strain.

In certain embodiments, the strain selected has a typical content in the plant as a whole, or in an extractable portion thereof, of major cannabinoids, minor cannabinoids, and selected terpenes that best approximates the predetermined composition of the active ingredient. In certain embodiments, the strain selected is one that is capable of providing an extract that best approximates the predetermined composition of the active ingredient. In specific embodiments, the strain selected has a typical content in the plant, extractable portion thereof, or extract thereof, that best approximates the predetermined weight ratios of desired major cannabinoids, minor cannabinoids, and optional selected terpenes. In specific embodiments, the strain selected has a typical content in the plant, extractable portion thereof, or extract thereof, that requires adjustment in concentration of the fewest number of the desired major cannabinoids, minor cannabinoids, and optional selected terpenes. In specific embodiments, the strain selected has a typical content in the plant, extractable portion thereof, or extract thereof, that requires the least expensive adjustment in concentration of the desired major cannabinoids, minor cannabinoids, and optional selected terpenes.

5.4.4. Product by Process

In typical embodiments, the pharmaceutically active ingredient is prepared by one of the processes described in Section 4.4.3 above.

In embodiments in which the pharmaceutically active ingredient is prepared from a starting compositional mixture by adjusting to predetermined desired final concentrations any one or more of the major cannabinoids, minor cannabinoids, and optional selected terpenes, all compounds in the active ingredient other than major cannabinoids, minor cannabinoids, and selected terpenes are present within the starting compositional mixture. In embodiments in which the starting compositional mixture is a *Cannabis sativa* extract, all compounds in the active ingredient other than the major cannabinoids, minor cannabinoids, and optional selected terpenes are present within the *Cannabis sativa* extract.

5.5. Pharmaceutical Compositions

In another aspect, pharmaceutical compositions are provided. The pharmaceutical composition comprises the pharmaceutically active ingredient disclosed herein and a pharmaceutically acceptable carrier or diluent.

5.5.1. Content of Pharmaceutically Active Ingredient

In typical embodiments, the active ingredient is present in the pharmaceutical composition at a concentration of at least 0.01 mg/ml, at least 0.1 mg/ml, at least 0.5 mg/ml, or at least 1 mg/ml. In certain embodiments, the active ingredient is present in the pharmaceutical composition at a concentration of at least 1 mg/ml, 2 mg/ml, 3 mg/ml, 4 mg/ml, 5 mg/ml, 10 mg/ml, 15 mg/ml, 20 mg/ml, or 25 mg/ml. In certain embodiments, the active ingredient is present in the pharmaceutical composition at a concentration of at least 30 mg/ml, 35 mg/ml, 40 mg/ml, 45 mg/ml or 50 mg/ml.

5.5.2. Formulation Generally

The pharmaceutical composition can be in any form appropriate for human or veterinary medicine, including a liquid, an oil, an emulsion, a gel, a colloid, an aerosol or a solid.

The pharmaceutical composition can be formulated for administration by any route of administration appropriate for human or veterinary medicine, including enteral and parenteral routes of administration.

In various embodiments, the pharmaceutical composition is formulated for administration by inhalation. In certain of these embodiments, the pharmaceutical composition is formulated for administration by a vaporizer. In certain of these embodiments, the pharmaceutical composition is formulated for administration by a nebulizer. In certain of these embodiments, the pharmaceutical composition is formulated for administration by an aerosolizer.

In various embodiments, the pharmaceutical composition is formulated for oral administration, for buccal administration, or for sublingual administration.

In some embodiments, the pharmaceutical composition is formulated for intravenous, intramuscular, or subcutaneous administration.

In some embodiments, the pharmaceutical composition is formulated for intrathecal or intracerebroventricular administration.

In some embodiments, the pharmaceutical composition is formulated for topical administration.

5.5.3. Pharmacological Compositions Adapted for Administration by Inhalation In some embodiments, unit dosage forms of the pharmaceutical composition described herein are provided that are adapted for administration of the pharmaceutical composition by vaporizer, nebulizer, or aerosolizer. In some embodiments, the dosage form is a vial, an ampule, optionally scored to allow user opening. In particular embodiments, the nebulizer is a jet nebulizer or an ultrasonic nebulizer.

Inhalable compositions are generally administered in an aqueous solution e.g., as a nasal or pulmonary spray. Preferred systems for dispensing liquids as a nasal spray are disclosed in U.S. Pat. No. 4,511,069. Such formulations may be conveniently prepared by dissolving compositions according to the present invention in water to produce an aqueous solution, and rendering the solution sterile. The formulations may be presented in multi-dose containers, for example in the sealed dispensing system disclosed in U.S. Pat. No. 4,511,069. Other suitable nasal spray delivery systems have been described in Transdermal Systemic Medication, Y. W. Chien Ed., Elsevier Publishers, New York, 1985; M. Naef et al. Development and pharmacokinetic characterization of pulmonal and intravenous delta-9-tetrahydrocannabinol (THC) in humans, J. PHARM. SCI. 93, 1176-84 (2004); and in U.S. Pat. Nos. 4,778,810; 6,080,762; 7,052,678; and 8,277,781 (each incorporated herein by reference). Additional aerosol delivery forms may include, e.g., compressed air-, jet-, ultrasonic-, and piezoelectric nebulizers, which deliver the biologically active agent dissolved or suspended in a pharmaceutical solvent, e.g., water, ethanol, or a mixture thereof.

Mucosal formulations are administered as dry powder formulations e.g., comprising the biologically active agent in a dry, usually lyophilized, form of an appropriate particle size, or within an appropriate particle size range, for intranasal delivery. Minimum particle size appropriate for deposition within the nasal or pulmonary passages is often about 0.5 micron mass median equivalent aerodynamic diameter (MMEAD), commonly about 1 micron MMEAD, and more typically about 2 micron MMEAD. Maximum particle size appropriate for deposition within the nasal passages is often about 10 micron MMEAD, commonly about 8 micron MMEAD, and more typically about 4 micron MMEAD. Intranasally respirable powders within these size ranges can be produced by a variety of conventional techniques, such as jet milling, spray drying, solvent precipitation, supercritical fluid condensation, and the like. These dry powders of appropriate MMEAD can be administered to a patient via a conventional dry powder inhaler (DPI) which rely on the patient's breath, upon pulmonary or nasal inhalation, to disperse the power into an aerosolized amount. Alternatively, the dry powder may be administered via air assisted devices that use an external power source to disperse the powder into an aerosolized amount, e.g., a piston pump.

5.5.4. Pharmacological Compositions Adapted for Oral/Buccal/Sublingual Administration Formulations for oral, buccal or sublingual administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a subject polypeptide therapeutic agent as an active ingredient. Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In solid dosage forms for oral, buccal or sublingual administration (capsules, tablets, pills, dragees, powders, granules, and the like), one or more therapeutic agents may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

5.5.5. Pharmacological Compositions Adapted for Injection

For intravenous, intramuscular, or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

In various embodiments, the unit dosage form is a vial, ampule, bottle, or pre-filled syringe. In some embodiments, the unit dosage form contains 0.01 mg, 0.1 mg, 0.5 mg, 1 mg, 2.5 mg, 5 mg, 10 mg, 12.5 mg, 25 mg, 50 mg, 75 mg, or 100 mg of the cannabinoid composition. In some embodiments, the unit dosage form contains 125 mg, 150 mg, 175 mg, or 200 mg of the cannabinoid composition. In some embodiments, the unit dosage form contains 250 mg of the cannabinoid composition.

In typical embodiments, the pharmaceutical composition in the unit dosage form is in liquid form. In various embodiments, the unit dosage form contains between 0.1 mL and 50 ml of the pharmaceutical composition. In some embodiments, the unit dosage form contains 1 ml, 2.5 ml, 5 ml, 7.5 ml, 10 ml, 25 ml, or 50 ml of pharmaceutical composition.

In particular embodiments, the unit dosage form is a vial containing 1 ml of the cannabinoid composition at a concentration of 0.01 mg/ml, 0.1 mg/ml, 0.5 mg/ml, or 1 mg/ml. In some embodiments, the unit dosage form is a vial containing 2 ml of the cannabinoid composition at a concentration of 0.01 mg/ml, 0.1 mg/ml, 0.5 mg/ml, or 1 mg/ml.

In some embodiments, the pharmaceutical composition in the unit dosage form is in solid form, such as a lyophilate, suitable for solubilization.

Unit dosage form embodiments suitable for subcutaneous, intradermal, or intramuscular administration include preloaded syringes, auto-injectors, and autoinject pens, each containing a predetermined amount of the pharmaceutical composition described hereinabove.

In various embodiments, the unit dosage form is a preloaded syringe, comprising a syringe and a predetermined amount of the pharmaceutical composition. In certain preloaded syringe embodiments, the syringe is adapted for subcutaneous administration. In certain embodiments, the syringe is suitable for self-administration. In particular embodiments, the preloaded syringe is a single use syringe.

In various embodiments, the preloaded syringe contains about 0.1 mL to about 0.5 mL of the pharmaceutical composition. In certain embodiments, the syringe contains about 0.5 mL of the pharmaceutical composition. In specific embodiments, the syringe contains about 1.0 mL of the pharmaceutical composition. In particular embodiments, the syringe contains about 2.0 mL of the pharmaceutical composition.

In certain embodiments, the unit dosage form is an autoinject pen. The autoinject pen comprises an autoinject pen containing a pharmaceutical composition as described herein. In some embodiments, the autoinject pen delivers a predetermined volume of pharmaceutical composition. In other embodiments, the autoinject pen is configured to deliver a volume of pharmaceutical composition set by the user.

In various embodiments, the autoinject pen contains about 0.1 mL to about 5.0 mL of the pharmaceutical composition. In specific embodiments, the autoinject pen contains about 0.5 mL of the pharmaceutical composition. In particular embodiments, the autoinject pen contains about 1.0 mL of the pharmaceutical composition. In other embodiments, the autoinject pen contains about 5.0 mL of the pharmaceutical composition.

5.5.6. Pharmacological Compositions Adapted for Topical Administration

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Suitable topical formulations include those in which the cannabinoid-containing complex mixtures featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearoylphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). The cannabinoid-containing complex mixtures featured in the invention may be encapsulated within liposomes or may form complexes thereto, in particular to cationic liposomes. Alternatively, the cannabinoid-containing complex mixtures may be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a C1-10 alkyl ester (e.g., isopropylmyristate IPM), monoglyceride, diglyceride or pharmaceutically acceptable salt thereof.

5.6. Dose Ranges, Generally

In vivo and/or in vitro assays may optionally be employed to help identify optimal dosage ranges for use. The precise dose to be employed in the formulation will also depend on the route of administration, and the seriousness of the condition, and should be decided according to the judgment of the practitioner and each subject's circumstances. Effective doses may be extrapolated from dose-response curves derived from in vitro or animal model test systems.

5.7. Unit Dosage Forms

The pharmaceutical compositions may conveniently be presented in unit dosage form.

The unit dosage form will typically be adapted to one or more specific routes of administration of the pharmaceutical composition.

In various embodiments, the unit dosage form is adapted for administration by inhalation. In certain of these embodiments, the unit dosage form is adapted for administration by a vaporizer. In certain of these embodiments, the unit dosage form is adapted for administration by a nebulizer. In certain of these embodiments, the unit dosage form is adapted for administration by an aerosolizer.

In various embodiments, the unit dosage form is adapted for oral administration, for buccal administration, or for sublingual administration.

In some embodiments, the unit dosage form is adapted for intravenous, intramuscular, or subcutaneous administration.

In some embodiments, the unit dosage form is adapted for intrathecal or intracerebroventricular administration.

In some embodiments, the pharmaceutical composition is formulated for topical administration.

The amount of active ingredient which can be combined with a carrier material to produce a single dosage form will generally be that amount of the compound which produces a therapeutic effect.

5.8. Methods of Use

5.8.1. Methods of Treating Neurodegenerative Diseases

In another aspect, methods are presented for treating a subject having a disease responsive to the cannabinoid-containing complex mixtures described herein. The method comprises administering to the subject a therapeutically effective amount of cannabinoid-containing complex mixtures described herein.

In certain embodiment, the disease responsive to an active ingredient described herein is a disease of the brain or central nervous system (CNS). In some embodiments, the disease is a neurodegenerative disease. In some embodiments, the disease is Alzheimer's disease, Parkinson's disease, Lewy Body Dementia, or Huntington's disease.

In typical embodiments, the cannabinoid-containing complex mixtures are administered in the form of a pharmaceutical composition as described above. These methods are particularly aimed at therapeutic and prophylactic treatments of animals, and more particularly, humans.

The terms "treatment", "treating", and the like are used herein to generally mean obtaining a desired pharmacologic and/or physiologic effect. The effect may be prophylactic, in terms of completely or partially preventing a disease, condition, or symptoms thereof, and/or may be therapeutic in terms of a partial or complete cure for a disease or condition and/or adverse effect, such as a symptom, attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms). Improvements in any conditions can be readily assessed according to standard methods and techniques known in the art. The population of subjects treated by the method of the disease includes subjects suffering from the undesirable condition or disease, as well as subjects at risk for development of the condition or disease.

By the term "therapeutically effective dose" or "effective amount" is meant a dose or amount that produces the desired effect for which it is administered. The exact dose or amount will depend on the purpose of the treatment, and will be ascertainable by one skilled in the art using known techniques (see, e.g., Lloyd (1999) The Art, Science and Technology of Pharmaceutical Compounding).

The term "sufficient amount" means an amount sufficient to produce a desired effect.

The term "therapeutically effective amount" is an amount that is effective to ameliorate a symptom of a disease. A therapeutically effective amount can be a "prophylactically effective amount" as prophylaxis can be considered therapy.

The term "ameliorating" refers to any therapeutically beneficial result in the treatment of a disease state, e.g., a neurodegenerative disease state, including prophylaxis, lessening in the severity or progression, remission, or cure thereof.

The actual amount administered, and rate and time-course of administration, will depend on the nature and severity of disease being treated. Prescription of treatment, e.g. decisions on dosage etc., is within the responsibility of general practitioners and other medical professionals, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

In some embodiments, the pharmaceutical composition is administered by inhalation, orally, by buccal administration, by sublingual administration, by injection or by topical application.

In some embodiments, the pharmaceutical composition is administered in an amount sufficient to modulate survival of neurons or dopamine release. In some embodiments, the major cannabinoid is administered in an amount less than 1 g, less than 500 mg, less than 100 mg, less than 10 mg per dose.

In some embodiments, the pharmaceutical composition is administered once a day, 2-4 times a day, 2-4 times a week, once a week, or once every two weeks.

A composition can be administered alone or in combination with other treatments, either simultaneously or sequentially dependent upon the condition to be treated.

Current inventions provide novel compositions comprising major cannabinoid and sub-mixtures. We have demonstrated that the compositions have significant physiological effects of neuro-protection and stimulation of dopamine release and thereby, they can have therapeutic effects on PD, which are well known to involve dopamine deficiencies and dopaminergic cell death during the progression of the diseases. Furthermore, we have identified specific combinations of major cannabinoid and sub-mixtures that exert significant synergistic effects. This invention further provides methods of treating PD and other neurodegenerative diseases using the pharmacological compositions identified herein.

5.9. Examples

The following examples are provided by way of illustration not limitation.

5.9.1. Example 1: Neuroprotective Effects of Cannabinoid-Containing Complex Mixtures Neuroprotective effects of (i) each major cannabinoid, (ii) each minor cannabinoid, (iii) each selected terpene, (iv) sub-mixtures (ENT) 1-12, and (v) each ENT mixture in combination separately with each of the two major cannabinoids, were assessed based on protection against neuronal cell death induced by 1-methyl-4-phenylpyridinium (MPP). MPP is an active metabolite of MPTP (1-methyl-4-phenyl-1,2,3,6-tetrahydropyridine) that is known to cause human Parkinsonism after injection. It is well known that MPP is taken up into dopaminergic neurons, interferes with oxidative phosphorylation in the mitochondria, reduces dopamine levels, and gradually causes cell death. MPP has been commonly used for cellular assays for agents that are effective in treating Parkinson's disease.

The MPP assay was performed in vitro on Cath.a cells, a CNS catecholaminergic cell line. Cells were cultured according to ATCC guidance, see https://www.atcc.org/Products/All/CRL-11179.aspx, and were induced to CAD differentiated status by serum deprivation (0.5% FBS culture for 36 h) prior to experiments essentially as described in Qi et al., *J. Neuroscience,* 17(4):1217-1225 (1997).

Neuroprotective effects were tested by applying each compound or mixture of compounds to the cell cultures 18 h after application of MPP. Cell viability was assessed 24 h after exposure to MPP, which is 6 h after exposure to the tested compound or compound mixture.

Neuroprotective effects of each individual compound were tested at 3 different concentrations, as described in FIGS. 1A-B. In the figures, protective effects of the compounds are presented as % rescue from MPP-induced cell death as compared to the control (no added compound). Each data point represents an average of twenty four experimental results obtained at a specific concentration (1, 10, or 100 μM) of each major or minor cannabinoid. Twenty four experimental results were obtained by repeating eight independent experiments three times on three different days ("8×3").

Major and minor cannabinoids showed some neuroprotective effects at 10 μM or 100 μM concentrations. However, most of the selected terpenes did not show any detectable neuroprotective effects, even at 100 μM concentration.

Neuroprotective effects of sub-mixtures comprising minor cannabinoids and/or selected terpenes (ENT 1-12) were also tested. The compositions of ENT1-12 are described in FIG. 2. In each experiment, the ENT mixture was applied so that the final molar concentration of each ingredient of the ENT mixture becomes 10 μM. Each ENT was tested in the absence of a major cannabinoid, with 10 µM (final concentration) CBD, and with 10 µM (final concentration) CBN. Their neuroprotective effects were tested and analyzed as described above and presented in FIGS. 3A-3B.

In FIG. 3A, the "Actual Effects" columns present the actual experimental data measuring protective effects of the sub-mixtures (ENT 1-12) with "No Major Cannabinoid", with "Cannabidiol (10 µM)", and with "Cannabinol (10 µM)". Each data point represents an average of twenty four (8×3) independent experiments conducted at 10 µM concentration of each ingredient. Standard deviations are presented in brackets. The "Sum of individual effects" columns provide the calculated sum of protective effects observed with individual ingredients of the respective sub-mixtures (see FIGS. 1A and 1B), either with "No Major Cannabinoid", with "Cannabidiol (10 µM)", or with "Cannabinol (10 µM)". The "Sum of individual effects" estimates the protective effect if the effects of the individual compounds were independent and strictly additive.

The data in FIGS. 3A-3B demonstrate synergistic effects of certain sub-mixtures when applied in the absence of a major cannabinoid.

For example, ENT8 (cannabichromene and cannabidivarin) without a major cannabinoid reduced MPP-induced cytotoxicity by 23%, while the sum of protective effects of its individual ingredients was only 10%. Analogously, ENT1 (comprising all 3 minor cannabinoids and all 5 selected terpenes) reduced MPP-induced toxicity by 37%, while the sum of effects of its individual ingredients was 12%. ENT10 (all 3 minor cannabinoids and two selected terpenes, limonene and linalool) reduced MPP-induced toxicity by 31%, while the sum of rescue effects of its individual ingredients is only 12%. The differences between the actual effects of cannabinoid and sub-mixtures and the calculated sum of individual effects (see, double-head arrow in FIG. 3B) represents synergistic effects.

Greater synergistic effects were observed when ENT mixtures were applied together with a major cannabinoid. The results are presented in FIG. 3A, in the fifth column for ENT plus cannabidiol, and the seventh column for ENT and cannabinol, respectively. The sums of rescue effects of its individual ingredients are also presented for comparison.

The data are also presented as a line graph in FIG. 3B. The solid line in FIG. 3B shows "Actual Effects" data illustrating protective effects of sub-mixtures (ENT 1-12) with or without major cannabinoid (CBN or CBD), as measured in the MPP assay. The dotted line shows the "Sum of individual effects," the sum of protective effects of individual ingredients of the mixtures, based on the data presented in FIGS. 1A-1B. The distance between the lines, indicated with a bidirectional arrow, is a measure of synergy.

We have identified several compositions that reduce MPP-induced cytotoxicity more than 50%: for example, ENT10+cannabidiol reduces toxicity 64%; ENT1+cannabidiol reduces cytotoxicity 62%; ENT6+cannabidiol reduces cytotoxicity 51%; and ENT10+cannabinol provides 51% rescue. The degree of protection was significantly higher than the sum of individual effects: for example, the sum of individual ingredient effects was only 26% for ENT10+cannabidiol; 26% for ENT1+cannabidiol; 24% for ENT6+cannabidiol; and 17% for ENT10+cannabinol (FIGS. 3A-B).

These data predict efficacy of these compositions in preventing or reducing neurodegeneration in Parkinson's disease and other neurodegenerative disorders. Moreover, efficacy is observed in the absence of THC.

5.9.2. Example 2: Dopamine Release Effects of Cannabinoid-Containing Complex Mixtures We selected certain compositions showing higher neuroprotective effects in Example 1 and tested their effects on dopamine release from PC12 cells.

We collected supernatant samples from 3 replicate wells 30 mins after application of PMA/Ionomycin (positive control) or test compositions, and measured dopamine in the medium using the Dopamine ELISA kit from Abnova (http://www.abnova.com/protocol_pdf/KA1887.pdf). PMA/Ionomycin is well known to be pro-secretory (a secretagogue) through the activation of multiple intracellular kinase pathways (PMA) and raising intracellular levels of free calcium (Ionomycin).

The test results are presented in FIG. 4 as percentage increase in secretion, relative to PMA/Ionomycin. The "No Major Cannabinoid" column provides data illustrating dopamine release effects of sub-mixtures in the absence of major cannabinoid. The "Cannabidiol (10 µM)" column provides data illustrating dopamine release effects of one of the respective sub-mixture in combination with 10 µM of cannabidiol. The "Cannabinol (10 µM)" column provides data illustrating dopamine release effects of the indicated sub-mixtures in combination with 10 µM of cannabinol.

The amounts of dopamine release in response to different compositions are presented as % compared to the amount of dopamine release in response to PMA/Ionomycin (positive control).

The ENT and/or major cannabinoid compositions significantly increased dopamine release. For example, ENT1+cannabidiol has 146%, ENT8+Cannabidiol has 138%, ENT1 alone has 131% and ENT1+cannabinol has 131% of the stimulation effects of PMA/Ionomycin.

5.9.3. Example 3: Development of a Calcium Influx Counter-Screen

A number of research studies suggest that effective therapeutics for PD should target not only restoration of dopamine production, but also address calcium-overload induced cell death. See, e.g., Cali et al., *Cell Tissue Res.* 357(2):439-54 (2014); Kang et al., *Nature* Communications 3, Article number: 1146 (2012).

We therefore studied susceptibility of HEK wild type cells, TRPV1 overexpressing HEK cells, and Cath.a cells to TRPV1-induced calcium-mediated cell death.

Cells were plated into tissue culture dishes and treated with either vehicle (HEK wild type and Cath.a) or tetracycline (1 micromolar) for 16 h to induce TRPV1 expression (HEK-TRPV1) at 37° C. in a 95% $CO_2$ atmosphere. After washing, media were replaced with a modified sodium Ringer solution containing 3% FBS and either 10 millimolar $CaCl_2$ or zero added $CaCl_2$ and 1 millimolar EGTA. Cells were then stimulated with either vehicle or capsaicin (1 µM) for 80 min prior to detachment with a cell scraper and resuspension in media with 10% (v/v) Trypan Blue. After 2 minutes, aliquots of 7 microliters of cell suspension were counted in a hemocytometer and field of at least 200 cells were scored for Trypan Blue positive or negative status.

FIGS. 6A and 6B show that TRPV1 can mediate calcium-dependent cell death in Cath.a neurons. FIG. 6A graphs cell death (measured by trypan blue positivity) at 80 min in the presence of 10 mM external $CaCl_2$ in HEK wild type cells, HEK cells transfected with a TRPV1 expression construct, and Cath.a cells, in each case in the absence of stimulation (left bar) and 80 minutes after stimulation with 250 nM capsaicin (right bar), showing that capsaicin can induce cell death in Cath.a cells. FIG. 6B graphs cell death (percent trypan blue positive cells) at 80 minutes in the absence of external calcium in HEK wild type cells, HEK cells transfected with a TRPV1 expression construct, and Cath.a cells, in each case in the absence of stimulation (left bar) and 80 minutes after stimulation with 250 nM capsaicin (right bar), confirming that capsaicin-induced death of Cath.a cells shown in FIG. 6A is dependent upon the presence of external calcium.

To assess the potential for cannabinoid-containing complex mixtures to trigger TRPV1 calcium influx and potential cell death, we prepared a complex mixture of cannabinoids and terpenes, the Strain A Mixture, based upon the actual chemo-profile of a *Cannabis sativa* cultivar currently used medicinally in Nevada, USA. The actual chemo-profile was modified in the Strain A Mixture by deliberate omission of THC and THCA and omission of certain labile or insoluble components.

The HEK293 cell line was stably transfected with the pcDNA6TR (Invitrogen, Calif.) plasmid (encoding the tetracycline-sensitive TREx repressor protein), and was maintained in DMEM+10% fetal bovine serum (inactivated at 55° C. for 1 h)+2 mM glutamine in humidified 5% $CO_2$ atmosphere at 37° C. Selection pressure on the TRex 293 cells was maintained by continuous culture in 10 μg/ml Blasticidin (Sigma, St Louis, Mo.).

For production of TRex HEK293 cells with inducible expression of TRPV1, parental cells were electroporated with the rat TRPV1 cDNA in the pcDNA4TO vector and clonal cell lines were selected by limiting dilution in the presence of 400 μg/ml zeocin (Invitrogen, Calif.). TRPV1 expression was induced using 1 μg/ml tetracycline for 16 h at 37° C. Stable lines were screened for inducible protein expression using anti-FLAG Western blot, and inducible expression was confirmed. Electrophysiological measurements further confirmed the presence and I/V curve 'signature' of TRPV1 in these induced cells.

Calcium responses mediated by TRPV1 were tested by calcium assay in the cell culture system. Cells were washed and incubated with 0.2 μM fluo-4 acetoxymethyl ester ("Fluo-4") for 30 minutes at 37° C. in a standard modified Ringer's solution of the following composition (in mM): NaCl 145, KCl 2.8, CsCl 10, CaCl2 10, MgCl2 2, glucose 10, Hepes.NaOH 10, pH 7.4, 330 mOsm. Cells were transferred to 96-well plates at 50,000 cells/well and stimulated as indicated. Calcium signals were acquired using a Flexstation 3 (Molecular Devices, Sunnydale, USA). Data was analyzed using SoftMax® Pro 5 (Molecular Devices). Where indicated, nominally calcium-free external conditions were achieved by the preparation of 0 mM $CaCl_2$ Ringer solution containing 1 mM EGTA. Where indicated, capsaicin (10 μM) and ionomycin (500 nM) were used as positive controls to induce calcium responses. Capsazepine (10 μM) was used where indicated to specifically antagonize TRPV1-mediated calcium responses. Where indicated, baseline traces (no stimulation, NS) were subtracted. Where indicated, vehicle alone traces were subtracted. Where indicated, vehicle comprising various diluents matched to corresponding mixtures was used as a negative control.

TRPV1-mediated calcium influx into HEK cells and HEK cells expressing TRPV1 was tested in response to the Strain A Mixture. FIG. 7 presents calcium flux data measured as Fluo-4 relative fluorescence unit (Fluo-4 RFU) over time (sec). As provided in FIG. 7, significant TRPV1-mediated calcium fluxes were observed in response to application of the Strain A Mixture.

These data demonstrate that cannabinoid-containing complex mixtures for the treatment of neurodegenerative diseases, and in particular cannabinoid-containing complex mixtures intended to preserve dopaminergic cell function and viability, should be counter-screened for their ability to trigger TRPV1-mediated calcium influx, and designed to omit or to contain at reduced levels cannabinoids and terpenes that trigger TRPV1-dependent calcium influx.

5.9.4. Example 4: Counter-Screening of Cannabinoid-Containing Complex Mixtures

Sub-mixtures (ENT) 1-12, and each ENT mixture in combination separately with each of the two major cannabinoids, is assessed for calcium-mediated influx into HEK cells and HEK cells expressing TRPV1 as described in Example 3, and are demonstrated to trigger minimal TRPV1-mediated calcium influx. In particular, ENT1+cannabidiol, ENT8+Cannabidiol, ENT1 alone, and ENT1+cannabinol are demonstrated to trigger minimal TRPV1-mediated calcium influx.

6. INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

7. EQUIVALENTS

The present disclosure provides, inter alia, compositions of cannabinoid-containing complex mixtures. The present disclosure also provides method of treating neurodegenerative diseases by administering the cannabinoid-containing complex mixtures. While various specific embodiments have been illustrated and described, the above specification is not restrictive. It will be appreciated that various changes can be made without departing from the spirit and scope of the invention(s). Many variations will become apparent to those skilled in the art upon review of this specification.

What is claimed is:
1. A method of treating Parkinson's disease, the method comprising:
administering to a patient with Parkinson's disease an effective amount of a pharmaceutical composition comprising:
as an active ingredient, a mixture comprising
the minor cannabinoids cannabichromene, cannabigerol, and cannabidivarin, and
the selected terpenes limonene, linalool, nerolidol, pinene, and phytol; and
a pharmaceutically acceptable carrier or diluent.
2. The method of claim 1, wherein the active ingredient mixture further includes a major cannabinoid, wherein the major cannabinoid is cannabidiol (CBD) or cannabinol (CBN).
3. The method of claim 2, wherein the major cannabinoid is cannabidiol (CBD).
4. The method of claim 2, wherein the major cannabinoid is cannabinol (CBN).

* * * * *